United States Patent
Cao

(10) Patent No.: US 9,376,393 B2
(45) Date of Patent: Jun. 28, 2016

(54) QUINOLINE COMPOUNDS WHICH ARE ANTI-ANGIOGENIC INTEGRIN ALPHA5 BETA1 INHIBITORS FOR USE IN THE TREATMENT OF FIBROSIS OR FIBROSIS-RELATED DISEASES

(71) Applicant: Clanotech AB, Solna (SE)

(72) Inventor: Yihai Cao, Bromma (SE)

(73) Assignee: Clanotech AB, Solna (SE)

( * ) Notice: Subject to any disclaimer, the term of this patent is extended or adjusted under 35 U.S.C. 154(b) by 0 days.

(21) Appl. No.: 14/370,315

(22) PCT Filed: Jan. 4, 2013

(86) PCT No.: PCT/SE2013/050003
§ 371 (c)(1),
(2) Date: Jul. 2, 2014

(87) PCT Pub. No.: WO2013/103317
PCT Pub. Date: Jul. 11, 2013

(65) Prior Publication Data
US 2015/0031723 A1 Jan. 29, 2015

Related U.S. Application Data

(60) Provisional application No. 61/583,353, filed on Jan. 5, 2012.

(51) Int. Cl.
| | | |
|---|---|---|
| *A61K 31/47* | (2006.01) | |
| *C07D 215/54* | (2006.01) | |
| *A61K 31/4706* | (2006.01) | |
| *A61K 45/06* | (2006.01) | |

(52) U.S. Cl.
CPC ............. *C07D 215/54* (2013.01); *A61K 31/47* (2013.01); *A61K 31/4706* (2013.01); *A61K 45/06* (2013.01)

(58) Field of Classification Search
CPC ... A61K 31/47; A61K 31/4706; A61K 45/06; A61P 35/00; C07D 215/54
See application file for complete search history.

(56) References Cited

U.S. PATENT DOCUMENTS

| | | | | |
|---|---|---|---|---|
| 8,557,843 | B2 * | 10/2013 | Westman et al. ............. | 514/313 |
| 8,957,092 | B2 * | 2/2015 | Westman et al. ............. | 514/313 |
| 2011/0257223 | A1 | 10/2011 | Goor et al. | |

FOREIGN PATENT DOCUMENTS

| | | |
|---|---|---|
| WO | WO-2005/090329 | 9/2005 |
| WO | 2008/119771 * | 10/2008 |
| WO | WO-2009/063070 | 5/2009 |
| WO | WO-2010/040992 | 4/2010 |
| WO | 2010/133669 * | 11/2010 |
| WO | WO-2010/133669 | 11/2010 |
| WO | WO-2010/133672 | 11/2010 |

OTHER PUBLICATIONS

Ou, International Immunopharmacology, vol. 9, pp. 70-79, 2009.*
Huang et al., "Integrin expression and function in the response of primary culture hepatic stellate cells to connective tissue growth factor (CCN2)", J Cell Mol Med., May 2011, pp. 1087-1095, vol. 15, No. 5.
Friedlander, "Fibrosis and diseases of the eye", J. Clin. Invest., Mar. 2007, pp. 576-586, vol. 117, No. 3.
Li et al., "Integrin α5β1 Mediates Attachment, Migration, and Proliferation in Human Retinal Pigment Epithelium: Relevance for Proliferative Retinal Disease", Invest Ophthalmol Vis Sci., Dec. 2009, pp. 5988-5996, vol. 50, No. 12.
Loubaki et al., "Crosstalk between T cells and bronchial fibroblasts obtained from asthmatic subjects involves CD40L/α5β1 interaction", Molecular Immunology, 2010, pp. 2112-2118, vol. 47.
Magro et al., "Immunohistochemical expression and distribution of alpha2beta1, alpha6beta1, alpha5beta1 integrins and their extracellular ligands, type IV collagen, laminin and fibronectin in palmar fibromatosis", Gen Diagn Pathol., Dec. 1997, pp. 203-208, vol. 143, No. 4.
Milliano et al., "Initial signaling of the fibronectin receptor (a5b1 integrin) in hepatic stellate cells is independent of tyrosine phosphorylation", J. Hepatol., 2003, pp. 32-37, vol. 39, No. 1.
Thannickal et al., "Myofibroblast Differentiation by Transforming Growth Factor-β1Is Dependent on Cell Adhesion and Integrin Signaling via Focal Adhesion Kinase", J. Biol. Chem., 2003, pp. 12384-12389, vol. 278, No. 14.
Wagrowska-Danilewicz, et al., "Expression of α5β1 and α6β1 integrins in IgA nephropathy (IgAN) with mild and severe proteinuria. An immunohistochemical study", Int Urol Nephrol., 2004, pp. 81-87, vol. 36, No. 1.
Wu et al., "The expression of integrin alpha5beta1 and transforming growth factor-beta in pulmonary fibrosis of rat", Zhonghua Bing Li Xue Za Zhi (Chin. J. Pathol.), Dec. 1999, pp. 427-431, vol. 28, No. 6 (article in Chinese).
Wu et al., "The expression of integrin alpha5betal and transforming growth factor-beta in pulmonary fibrosis of rat", Zhonghua Bing Li Xue Za Zhi (Chin. J. Pathol.), Dec. 1999, pp. 427-431, vol. 28, No. 6 (summary in English).
Wynn, "Fibrotic Disease and the $T_H1/T_H2$ Paradigm", Nature Reviews Immunology, Aug. 2004, pp. 583-594, vol. 4.
Zahn et al., "Assessment of the Integrin α5β1 Antagonist JSM6427 in Proliferative Vitreoretinopathy Using In Vitro Assays and a Rabbit Model of Retinal Detachment", Invest Ophthalmol Vis Sci., Feb. 2010, pp. 1028-1035, vol. 51, No. 2.

* cited by examiner

*Primary Examiner* — D M Seaman
(74) *Attorney, Agent, or Firm* — White & Case LLP

(57) ABSTRACT

A new medical therapy, and more particularly certain quinoline compounds which are anti-angiogenic integrin aplha5beta1 inhibitors, for use in the treatment of fibrosis, or a fibrosis-related disease, such as a fibrotic disease affecting the lung, liver, kidney, skin, epidermis, endodermis, muscle, tendon, cartilage, heart, stomach, large intestine, small intestine, colon, uterus, nervous system, testis, adrenal gland, artery, vein, biliary tract, or eye.

12 Claims, No Drawings

QUINOLINE COMPOUNDS WHICH ARE ANTI-ANGIOGENIC INTEGRIN ALPHA5 BETA1 INHIBITORS FOR USE IN THE TREATMENT OF FIBROSIS OR FIBROSIS-RELATED DISEASES

FIELD OF THE INVENTION

The present invention is directed to a new medical therapy, and more particularly to certain quinoline compounds for use the treatment of fibrosis or a fibrosis-related disease.

BACKGROUND

Tissue fibrosis (scarring) is a leading cause of morbidity and mortality. Current treatments for fibrotic disorders, such as idiopathic pulmonary fibrosis, hepatic fibrosis and systemic sclerosis, target the inflammatory cascade, but they have been widely unsuccessful, largely because the mechanisms that are involved in fibrogenesis are now known to be distinct from those involved in inflammation (Wynn, T. 2004: Nat. Rev. Immunol. 4(8): pp. 583-594).

Repair of damaged tissues is a fundamental biological process that allows the ordered replacement of dead or injured cells during an inflammatory response, a mechanism that is crucial for survival. Tissue damage can result from several acute or chronic stimuli, including infections, autoimmune reactions and mechanical injury. The repair process involves two distinct stages: a regenerative phase, in which injured cells are replaced by cells of the same type and there is no lasting evidence of damage; and a phase known as fibroplasia or fibrosis, in which connective tissue replaces normal parenchymal tissue. In most cases, both stages are required to slow or reverse the damage caused by an injurious agent. However, although initially beneficial, the healing process can become pathogenic if it continues unchecked, leading to considerable tissue remodelling and the formation of permanent scar tissue. In some cases, it might ultimately cause organ failure and death. Fibrotic scarring is often defined as a wound-healing response that has gone awry (Wynn, T. 2004: Nat. Rev. Immunol. 4(8): pp. 583-594).

Fibroproliferative diseases are an important cause of morbidity and mortality worldwide. Fibrotic changes can occur in various vascular disorders, including cardiac disease, cerebral disease and peripheral vascular disease, as well as in all the main tissues and organ systems, including the skin, kidney, lung, eye, bladder, heart, joints, intestinal tissues, connective tissue, reproductive tissue, bone tissue and liver. Fibrosis is a troubling problem for an increasing number of individuals and is a common pathological sequela of many persistent inflammatory diseases, such as idiopathic pulmonary fibrosis, progressive kidney disease and liver cirrhosis (Wynn, T. 2004: Nat. Rev. Immunol. 4(8): pp. 583-594).

The United States government estimates that 45% of deaths in the United States can be attributed to fibrotic disorders. Fibrosis affects nearly all tissues and organ systems. Interstitial Lung Disease (ILD) characterised by pulmonary inflammation and fibrosis is an example of disorders in which fibrosis is a major cause of morbidity and mortality. ILD is known to have a number of causes such as sarcoidosis, silicosis, collagen vascular diseases, systemic sarcoderma. However, the causes of the common type of ILD such as idiopathic pulmonary fibrosis are unknown. Other organ fibrotic disorders include liver cirrhosis; liver fibrosis resulting from chronic hepatitis B and C infection; kidney disease; heart disease; diseases of the eye such as macular degeneration, and retinal and vitreal retinopathy; systemic and local scleroderma; keloids and hypertrophic scars; atherosclerosis and restenosis; surgical complications; chemotherapeutic drug-induced fibrosis; accidental injury; and burns (Wynn, T. 2004: Nat. Rev. Immunol. 4(8): pp. 583-594).

Wound healing and disregulated events leading to fibrosis both involve the proliferation and differentiation of certain cell types (tissue dependent), mainly fibroblasts to myofibroblasts and the deposition of extracellular matrix. Whether the fibroblasts are locally derived or if they are coming from a circulating precursor population is unclear. Fibrocytes are a distinct population of fibroblast-like cells that derive from peripheral blood monocytes that enter site of tissue injury to promote angiogenesis and wound healing.

The ocular response to hypoxia and inflammatory insults typically leads to retinal or choroidal neovascularization. During development, this process is highly regulated and leads to the establishment of a well organized, mature vasculature. In the adult eye, this is often not the case, and associated glial cells (e.g., astrocytes, and Mueller cells), microglia and RPE cells proliferate with the endothelial cells, leading to fibrosis and scar formation. The role of cell adhesion molecules, such as integrins, in regulating the relationship between proliferating vascular cells and their environment, has been the focus of many studies (Martin Friedlander Journal of Clinical Investigation http://www.jci.org Volume 117 Number 3 Mar. 2007).

There is ample evidence indicating the involvement of alpha5 beta1 integrin and extracelluar matrix interaction during fibroblast differentiation. High expression of alpha5 beta1 integrin is found in activated fibroblasts with strong accumulation of alpha5beta1 integrin when fibroblasts switch to the fibrotic state (Thannickal 2003, J. Biol. Chem. 278, 12384). High levels of alpha5 beta1 integrin were detected in proliferating fetal RPE cells, activated ARPE-19 cells (retinal pigmental cells) and in PVR membrane in patients with proliferative vitreoretinopathy (G Zahn et al. Invest Ophthalmol Vis Sci. 2010 1028-35; Rong Li et al Inv Ophth Vis Sci 2009, 50(12) 5988-5996). Integrin alpha5 beta1 plays a key role in inducing the activation, proliferation and differentiation of pulmonary fibroblasts (PFbs), causing an increase of extracellular matrix synthesis during pulmonary fibrogenesis. Strong integrin alpha5 beta1 integrin expression is seen in proliferated interstitial cells with fibroblast and myofibroblast differentiation. Changes in FN were similar to that of the alpha5 beta1 integrin. Expression of alpha5 beta1, fibronectin (FN)mRNAs and their relevant proteins increase in PFbs after TGF-beta1 administration. (Wu H, et al Zhonghua Bing Li Xue Za Zhi. 1999 December; 28(6):427-31 article in Chinese). Interaction of bronchial fibroblasts with T cells increases the production of profibrogenic cytokine IL-6. In asthmatic conditions this interaction involves CD40L alpha5 beta1 integrin. T cells and structural cells crosstalk in asthma may maintain local mucosal inflammation (Loubaki L, et al Mol Immunol. 2010 July; 47(11-12):2112-8). Moreover alpha5 beta1 integrin is expressed and restricted to the myofibroblast-rich cellular areas in palmar fibromatosis (Magro G. et al Gen Diagn Pathol. 1997 December; 143(4):203-8). Activation of hepatic stellate cells (HSC) plays an integral role in hepatic fibrosis. HSC activation increases the fibronectin alpha5 beta1 integrin receptor expression and the interactions between alpha5 beta1 integrin and fibronectin increases collagen synthesis. Production of connective tissue growth factor (CCN2) is a hallmark of hepatic fibrosis and regulates integrin expression in primary culture of hepatic stellate cells (HSC) and supports HSC adhesion via its binding of cell surface alpha5 beta1 integrin (Milliano M T et al. J Hepatol. 2003; 39(1):32-7, Huang G et al J Cell Mol Med. 2011;

15(5):1087-95). Positive association between the interstitial expression of alpha5 beta1 integrin and the relative interstitial cortical volume in renal biopsies in patients with mild and severe proteinuria suggests that alpha5 beta1 integrin may play a role in the pathogenesis of chronic progressive renal diseases. The intensity of interstitial alpha5 beta1 integrin immunoexpression positively correlates with the degree of interstitial fibrosis (Wagrowska-Danilewicz M et al. *Int Urol Nephrol.* 2004; 36(1):81-7).

Fibrotic traction of the retina in AMD is seen after anti-VEGF treatment and fibrotic lesion in both AMD and PDR results from neovascularization. Fibrotic lesions in AMD are not treatable with anti-VEGF and AMD patients non-responders to anti-VEGF are the patients with fibrotic lesions.

Currently treatments are available for fibrotic disorders including immune suppressive drugs such as corticosteroids, and other anti-inflammatory treatments. However the mechanism involved in the regulation of fibrosis appears to be distinct from those of inflammation, and anti-inflammatory treatment are not always effective in reducing and preventing fibrosis.

The fact that PDR patients are not treatable with current anti-angiogenic therapy (anti-VEGF) and that the AMD patients who are non-responders to anti-VEGF are those that have fibrotic lesions, indicate that a significant unmet medical need still remains particularly to reduce and prevent fibrosis and control fibrotic diseases.

WO 2009/063070, WO 2010/133669 and WO 2010/133672, disclose certain quinoline compounds which are anti-angiogenic integrin aplha5beta1 inhibitors, and their use in therapy.

SUMMARY OF THE INVENTION

An aspect of the present invention is a compound of Formula I

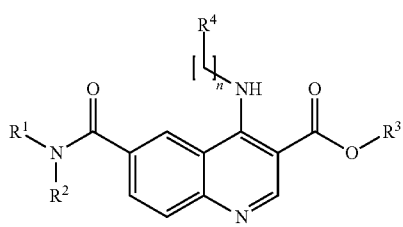

I wherein
n=0, 1 or 2;
$R^1$ and $R^2$ are each independently selected from hydrogen; saturated or unsaturated, branched or unbranched $C_{1-10}$ alkyl or $C_{3-12}$ cycloalkyl; and substituted or non-substituted phenyl or benzyl;
$R^3$ is hydrogen; or saturated or unsaturated, branched or unbranched $C_{1-10}$ alkyl or $C_{3-12}$ cycloalkyl;
$R^4$ is substituted or non-substituted $C_6$-$C_{10}$ aryl or $C_5$-$C_9$ heteroaryl wherein the heteroatoms independently are selected from N, O and S; or substituted or non-substituted mono- or bicyclic $C_{3-12}$ cycloalkyl or $C_5$-$C_9$ heterocyclyl wherein the heteroatoms are independently selected from N, O and S;
or a pharmaceutically acceptable salt thereof;
for use in the treatment of fibrosis, or a fibrosis-related disease.

One aspect of the present invention is a compound of Formula I, wherein $R^1$ and $R^2$ are each independently selected from hydrogen; $C_{1-4}$ alkyl; and $C_{3-4}$ cycloalkyl, for use in the treatment of fibrosis.

Still another aspect of the present invention is a compound of Formula I, wherein $R^1$ and $R^2$ are each independently selected from hydrogen and $C_{1-4}$ alkyl, for use in the treatment of fibrosis.

Still another aspect of the present invention is a compound of Formula I, wherein $R^1$ and $R^2$ are each independently selected from hydrogen and methyl, for use in the treatment of fibrosis.

Still another aspect of the present invention is a compound of Formula I, wherein $R^1$ is hydrogen, for use in the treatment of fibrosis.

Still another aspect of the present invention is a compound of Formula I, wherein $R^3$ is hydrogen or $C_{1-4}$ alkyl, for use in the treatment of fibrosis.

Still another aspect of the present invention is a compound of Formula I, wherein $R^4$ is substituted or unsubstituted phenyl, for use in the treatment of fibrosis.

Still another aspect of the present invention is a compound of Formula I, wherein n is 0 or 1, for use in the treatment of fibrosis.

Still another aspect of the present invention is a compound of Formula I, wherein n is 0, for use in the treatment of fibrosis.

Another aspect of the present invention is a compound of Formula II

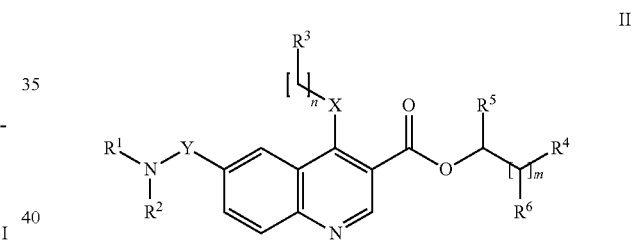

II wherein:
n is 0 (zero) or 1;
m is 0 (zero), 1 or 2;
$R^1$ and $R^2$ are each independently selected from hydrogen; branched or unbranched $C_1$-$C_8$ alkyl, $C_2$-$C_8$ alkenyl or $C_2$-$C_8$ alkynyl; monocyclic or bicyclic, saturated or unsaturated $C_3$-$C_8$ carbocyclyl; and monocyclic or bicyclic, saturated or unsaturated $C_3$-$C_7$ heterocyclyl wherein each heteroatom is independently selected from N, O and S; said alkyl, alkenyl, alkynyl, carbocyclyl or heterocyclyl optionally being substituted with 1, 2 or 3 groups $R^a$;
$R^3$ is selected from monocyclic or bicyclic $C_6$-$C_{10}$ aryl; and monocyclic or bicyclic $C_3$-$C_9$ heteroaryl or heterocyclyl, wherein in said heteroaryl and heterocyclyl each heteroatom is independently selected from N, O and S; said aryl, heteroaryl or heterocyclyl optionally being substituted with 1, 2, 3, 4 or 5 groups $R^b$;
$R^4$ is selected from —OC(O)$R^7$; —C(O)O$R^7$; —N$R^7R^8$; —C(O)N$R^7R^8$; monocyclic or bicyclic $C_3$-$C_9$ heteroaryl; and monocyclic or bicyclic, saturated or unsaturated $C_5$-$C_9$ heterocyclyl, wherein said heteroaryl and heterocyclyl optionally contains an oxo group in the ring, and wherein in said heteroaryl and heterocyclyl each heteroatom independently is selected from N, O and S; said heteroaryl and heterocyclyl optionally being substituted with 1, 2 or 3 groups $R^a$;

$R^5$ and W are each independently selected from hydrogen; and branched or unbranched $C_1$-$C_4$ alkyl, $C_2$-$C_4$ alkenyl or $C_2$-$C_4$ alkynyl; said alkyl, alkenyl and alkynyl optionally being substituted with 1, 2, or 3 groups independently selected from fluorine and chlorine;

$R^7$ is selected from hydrogen; and branched or unbranched $C_1$-$C_4$ alkyl, $C_2$-$C_4$ alkenyl or $C_2$-$C_4$ alkynyl; and phenyl; said alkyl, alkenyl, alkynyl and phenyl optionally being substituted with 1, 2, or 3 groups independently selected from fluorine and chlorine;

$R^8$ is selected from hydrogen; branched or unbranched $C_1$-$C_4$ alkyl, $C_2$-$C_4$ alkenyl or $C_2$-$C_4$ alkynyl; monocyclic or bicyclic $C_6$-$C_{10}$ aryl; —S(O)$_2$R$^9$; —C(O)OR$^9$; and —C(O)R$^{10}$; said alkyl, alkenyl, alkynyl or aryl optionally being substituted with 1, 2, or 3 halogen(s);

$R^9$ is selected from hydrogen and branched or unbranched $C_1$-$C_4$ alkyl, $C_2$-$C_4$ alkenyl or $C_2$-$C_4$ alkynyl; said alkyl, alkenyl and alkynyl optionally being substituted with 1, 2, or 3 groups independently selected from fluorine and chlorine;

$R^{10}$ is selected from hydrogen; branched or unbranched $C_1$-$C_4$ alkyl, $C_2$-$C_4$ alkenyl or $C_2$-$C_4$ alkynyl; and $C_6$ aryl; said aryl optionally being substituted with 1, 2 or 3 groups $R^a$; and said alkyl, alkenyl and alkynyl optionally being substituted with 1, 2, or 3 groups independently selected from fluorine and chlorine;

Y is selected from —C(O)—; —S(O)—; and —S(O)$_2$—;

X is selected from —NR$^c$—; —O—; and —S—;

each $R^a$ is independently selected from halogen; hydroxy; carbonyl; methoxy; halomethoxy; dihalomethoxy; and trihalomethoxy;

each $R^b$ is independently selected from halogen; carboxy; hydroxy; cyano; $C_1$-$C_4$ alkyl; $C_2$-$C_4$ alkenyl; $C_2$-$C_4$ alkynyl; $C_1$-$C_4$ alkyloxy; $C_2$-$C_4$ alkenyloxy; $C_2$-$C_4$ alkynyloxy; $C_1$-$C_4$ alkylthio; $C_2$-$C_4$ alkenylthio; $C_2$-$C_4$ alkynylthio; $C_1$-$C_4$ alkyl; $C_2$-$C_4$ alkenyl or $C_2$-$C_4$ alkynyl secondary or tertiary amino; $C_1$-$C_4$ alkyl, $C_2$-$C_4$ alkenyl or $C_2$-$C_4$ alkynyl secondary or tertiary amido; $C_1$-$C_4$ alkyl, $C_2$-$C_4$ alkenyl or $C_2$-$C_4$ alkynyl carbonyl; $C_1$-$C_4$ alkyl, $C_2$-$C_4$ alkenyl or $C_2$-$C_4$ alkynyl sulfonyl; $C_1$-$C_4$ alkyl, $C_2$-$C_4$ alkenyl or $C_2$-$C_4$ alkynyl sulfonyloxy; $C_1$-$C_4$ alkyl, $C_2$-$C_4$ alkenyl or $C_2$-$C_4$ alkynyl secondary or tertiary sulfonamido; $C_1$-$C_4$ alkyl, $C_2$-$C_4$ alkenyl or $C_2$-$C_4$ alkynyl silyl; and $C_1$-$C_4$ alkyloxy, $C_2$-$C_4$ alkenyloxy, or $C_2$-$C_4$ alkynyloxy carbonyl; wherein any alkyl, alkenyl and alkynyl moiety optionally is substituted with 1, 2 or 3 groups independently selected from halogen, hydroxy, methoxy, halomethoxy, dihalomethoxy and trihalomethoxy; and $R^c$ is selected from hydrogen; and branched or unbranched $C_1$-$C_4$ alkyl, $C_2$-$C_4$ alkenyl or $C_2$-$C_4$ alkynyl;

wherein any $C_p$ alkyl, alkynyl or alkenyl group having a number $p \geq 4$ of carbon atoms optionally includes a $C_q$ carbocyclic portion of q of carbon atoms, whereby $3 \leq q < p$;

or a pharmaceutically acceptable salt thereof;

for use in the treatment of fibrosis, or a fibrosis-related disease.

An aspect of the present invention is a compound of formula II, wherein $R^1$ and $R^2$ are each independently selected from hydrogen, $C_1$-$C_4$ alkyl, $C_2$-$C_4$ alkenyl and $C_2$-$C_4$ alkynyl, said alkyl, alkenyl, alkynyl, carbocyclyl or heterocyclyl optionally being substituted with 1, 2 or 3 groups $R^a$; $R^a$ is halogen, for use in the treatment of fibrosis.

An aspect of the present invention is a compound of formula II, wherein $R^1$ represents hydrogen and $R^2$ represents $C_1$-$C_4$ alkyl, for use in the treatment of fibrosis.

An aspect of the present invention is a compound of formula II, wherein Y is —C(O), for use in the treatment of fibrosis.

An aspect of the present invention is a compound of formula II, wherein n is 0, for use in the treatment of fibrosis.

An aspect of the present invention is a compound of formula II, wherein $R^3$ is phenyl, optionally substituted with 1, 2, 3, 4 or 5 groups $R^b$, for use in the treatment of fibrosis.

An aspect of the present invention is a compound of formula II, wherein $R^3$ is phenyl, optionally substituted with 1 group $R^b$, for use in the treatment of fibrosis.

An aspect of the present invention is a compound of formula II, wherein X is —NR$^c$—, for use in the treatment of fibrosis.

An aspect of the present invention is a compound of formula II, wherein $R^c$ is hydrogen, for use in the treatment of fibrosis.

An aspect of the present invention is a compound of formula II, wherein $R^4$ is selected from —OC(O)R$^7$; —C(O)OR$^7$; —NR$^7$R$^8$; and —C(O)NR$^7$R$^8$, for use in the treatment of fibrosis.

An aspect of the present invention is a compound of formula II, wherein $R^7$ is selected from $C_1$-$C_4$ alkyl and phenyl; $R^8$ is selected from $C_1$-$C_4$ alkyl, —S(O)$_2$R$^9$; —C(O)OR$^9$ and —C(O)R$^{10}$; $R^9$ represents $C_1$-$C_4$ alkyl; and $R^{10}$ represents phenyl, for use in the treatment of fibrosis.

An aspect of the present invention is a compound of formula II, wherein $R^4$ is monocyclic or bicyclic $C_5$-$C_9$ heteroaryl or monocyclic or bicyclic, saturated or unsaturated $C_3$-$C_9$ heterocyclyl, wherein each heteroatom is independently selected from N, O and S, for use in the treatment of fibrosis.

An aspect of the present invention is a compound of formula II, wherein $R^4$ is monocyclic $C_1$-$C_4$ heteroaryl; or monocyclic saturated or unsaturated $C_1$-$C_4$ heterocyclyl, wherein each heteroatom is independently selected from N, O and S, for use in the treatment of fibrosis.

An aspect of the present invention is a compound of formula II, wherein $R^4$ is monocyclic $C_1$-$C_4$ heteroaryl, wherein each heteroatom is independently selected from N, O and S, for use in the treatment of fibrosis.

An aspect of the present invention is a compound of formula II, wherein each $R^b$ is independently selected from $C_1$-$C_4$ alkyl, $C_2$-$C_4$ alkenyl or $C_2$-$C_4$ alkynyl, said alkyl, alkenyl and alkynyl, optionally being substituted with 1, 2 or 3 halogen(s), for use in the treatment of fibrosis.

An aspect of the present invention is a compound of formula II, wherein each $R^b$ is independently selected from $C_1$-$C_4$ alkyloxy, $C_2$-$C_4$ alkenyloxy and $C_2$-$C_4$ alkynyloxy, said alkyloxy, alkenyloxy and alkynyloxy optionally being substituted with 1, 2 or 3 halogen(s), for use in the treatment of fibrosis.

An aspect of the present invention is a compound of formula II, wherein each $R^b$ is selected from chloro, fluoro or trifluoromethyl, for use in the treatment of fibrosis.

An aspect of the present invention is a compound of formula II, wherein each $R^b$ is a halogen, for use in the treatment of fibrosis.

An aspect of the present invention is a compound of Formula III

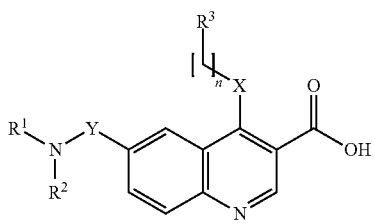

III wherein n is 0 (zero) or 1;

$R^1$ and $R^2$ are each independently selected from hydrogen; branched or unbranched $C_1$-$C_8$ alkyl, $C_2$-$C_8$ alkenyl, or $C_2$-$C_8$ alkynyl; monocyclic or bicyclic, saturated or unsaturated $C_3$-$C_8$ carbocyclyl; and monocyclic or bicyclic, saturated or unsaturated $C_3$-$C_7$ heterocyclyl wherein the heteroatoms are independently selected from N, O and S;

said alkyl, alkenyl, alkynyl, carbocyclyl or heterocyclyl optionally being substituted with 1, 2, or 3 groups $R^a$;

$R^3$ is selected from monocyclic or bicyclic $C_6$-$C_{10}$ aryl; and monocyclic or bicyclic $C_5$-$C_9$ heteroaryl, wherein the heteroatoms independently are selected from N, O and S;

said aryl or heteroaryl optionally being substituted with 1, 2, 3, 4 or 5 groups $R^b$;

Y is selected from —C(O)—; —S(O)—; and —S(O)$_2$—;

X is selected from —NR$^c$—; —O—; and —S—;

each $R^a$ is independently selected from halogen; hydroxy; carbonyl; methoxy; halomethoxy; dihalomethoxy; and trihalomethoxy;

each $R^b$ is independently selected from halogen, branched or unbranched $C_1$-$C_4$ alkyl, $C_2$-$C_4$ alkenyl or $C_2$-$C_4$ alkynyl; branched or unbranched $C_1$-$C_4$alkyloxy, $C_2$-$C_4$alkenyloxy or $C_2$-$C_4$ alkynyloxy; branched or unbranched $C_1$-$C_4$alkylthio, $C_2$-$C_4$alkenylthio or $C_2$-$C_4$alkynylthio; said alkyl, alkenyl, alkynyl, alkyloxy, alkenyloxy alkynyloxy, alkylthio, alkenylthio or alkynylthio group optionally being substituted with 1, 2 or 3 halogens;

$R^c$ is selected from hydrogen and branched or unbranched $C_1$-$C_4$ alkyl, $C_2$-$C_4$ alkenyl or $C_2$-$C_4$ alkynyl;

or a pharmaceutically acceptable salt thereof;

for use in the treatment of fibrosis, or a fibrosis-related disease.

An aspect of the present invention is a compound of formula III, wherein n is 0, for use in the treatment of fibrosis.

An aspect of the present invention is a compound of formula III, wherein $R^1$ and $R^2$ are each independently selected from hydrogen and branched or unbranched $C_1$-$C_8$ alkyl, $C_2$-$C_8$ alkenyl and $C_2$-$C_8$ alkynyl, said alkyl, alkenyl, or alkynyl optionally being substituted with 1, 2, or 3 groups $R^a$, for use in the treatment of fibrosis.

An aspect of the present invention is a compound of formula III, wherein $R^1$ and $R^2$ are each independently selected from hydrogen and branched or unbranched $C_1$-$C_8$ alkyl, said alkyl optionally being substituted with 1, 2, or 3 groups $R^a$, for use in the treatment of fibrosis.

An aspect of the present invention is a compound of formula III, wherein $R^1$ is hydrogen and $R^2$ is selected from $C_1$-$C_4$ alkyl, for use in the treatment of fibrosis.

An aspect of the present invention is a compound of formula III, wherein $R^3$ is phenyl, optionally substituted with 1, 2, 3, 4 or 5 groups $R^b$, for use in the treatment of fibrosis.

An aspect of the present invention is a compound of formula III, wherein Y is —C(O), for use in the treatment of fibrosis.

An aspect of the present invention is a compound of formula III, wherein X is —NR$^c$—, for use in the treatment of fibrosis.

An aspect of the present invention is a compound of formula III, wherein each $R^a$ is halogen, for use in the treatment of fibrosis.

An aspect of the present invention is a compound of formula III, wherein each $R^b$ is independently selected from halogen; and $C_1$-$C_4$ alkyl; and $C_1$-$C_4$ alkyloxy; wherein any alkyl or alkyloxy optionally is substituted with 1, 2 or 3 halogens, for use in the treatment of fibrosis.

An aspect of the present invention is a compound of formula III, wherein $R^c$ is hydrogen, for use in the treatment of fibrosis.

DETAILED DESCRIPTION OF THE INVENTION

Compounds of formula I, II or III as used in accordance with the present invention can be present as pharmaceutically acceptable salts.

Examples of pharmaceutically acceptable salts of compounds of formula I, II or III, useful as herein described, may form acid addition salts, e.g. at the amino function. These may be formed, for example, with strong inorganic acids, such as mineral acids, for example sulfuric acid, phosphoric acid or a hydrohalic acid; strong organic carboxylic acids, such as alkanecarboxylic acids of 1 to 4 carbon atoms which are unsubstituted or substituted, for example, by halogen, for example acetic acid, saturated or unsaturated dicarboxylic acids, for example oxalic, malonic, succinic, maleic, fumaric, phthalic or terephthalic acid, hydroxycarboxylic acids, for example ascorbic, glycolic, lactic, malic, tartaric or citric acid, amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center.

Compounds of formula I, II or III having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl, tertbutyl, diethyl, diisopropyl, triethyl, tributyl or dimethyl-propylamine, or a mono-, di- or trihydroxy lower alkylamine, for example mono-, di- or triethanolamine. Corresponding internal salts may furthermore be formed. Salts that are unsuitable for pharmaceutical uses but which can be employed, for example, for the isolation or purification of free compounds of formula I or their pharmaceutically acceptable salts are also included.

An example of a compound of Formula I useful in accordance with the present invention is a compound selected from any one of the following compounds Nos. I-1 to I-6:

| Comp. No. | Chemical Structure | Chemical Name |
|---|---|---|
| I-1 | 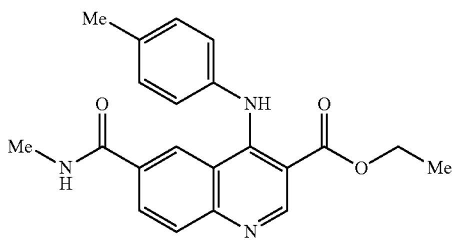 [SMILES: CCOC(=O)c1cnc2ccc(C(=O)NC)cc2c1Nc1ccc(C)cc1] | Ethyl 6-(methylcarbamoyl)-4-[(4-methylphenyl)amino]quinoline-3-carboxylate |
| I-2 | 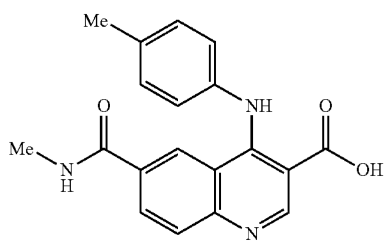 [SMILES: CNC(=O)c1ccc2ncc(C(=O)O)c(Nc3ccc(C)cc3)c2c1] | 6-Methylcarbamoyl-4-p-tolylamino-quinoline-3-carboxylic acid |
| I-3 | 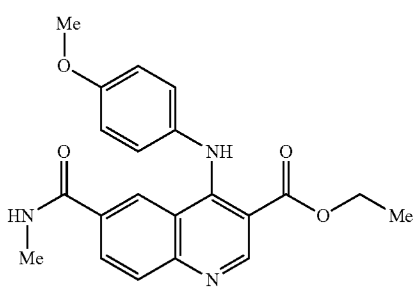 [SMILES: CCOC(=O)c1cnc2ccc(C(=O)NC)cc2c1Nc1ccc(OC)cc1] | Ethyl 4-[(4-methoxyphenyl)amino]-6-(methylcarbamoyl)quinoline-3-carboxylate |
| I-4 | 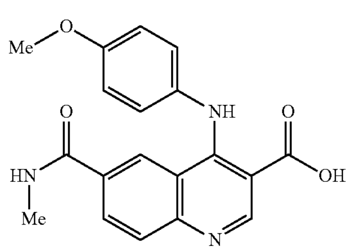 [SMILES: CNC(=O)c1ccc2ncc(C(=O)O)c(Nc3ccc(OC)cc3)c2c1] | 4-[(4-Methoxyphenyl)amino]-6-(methylcarbamoyl)quinoline-3-carboxylic acid |
| I-5 | 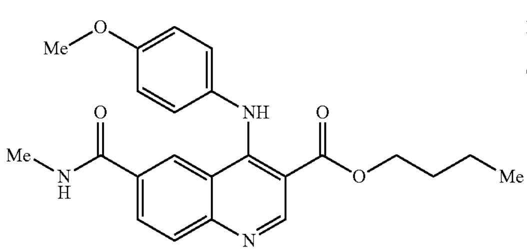 | Butyl 4-[(4-methoxyphenyl)amino]-6-(methylcarbamoyl)quinoline-3-carboxylate |
| I-6 | 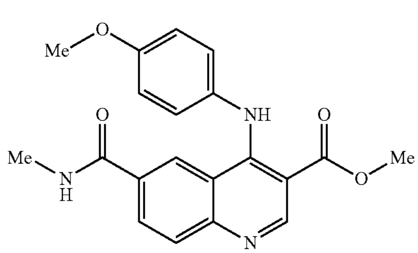 [SMILES: CNC(=O)c1ccc2ncc(C(=O)OC)c(Nc3ccc(OC)cc3)c2c1] | Methyl 4-[(4-methoxyphenyl)amino]-6-(methylcarbamoyl)quinoline-3-carboxylate |

An example of a compound of Formula II useful in accordance with the present invention is a compound selected from any one of the following compounds Nos. II-1 to II-15:

| Comp. No. | Chemical Structure | Chemical Name |
|---|---|---|
| II-1 | 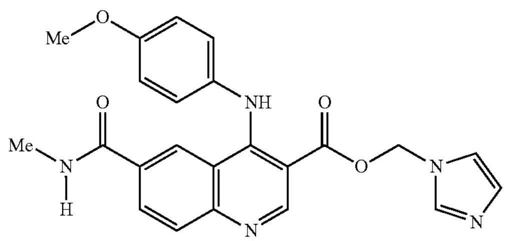 [SMILES: CNC(=O)c1ccc2ncc(C(=O)OCn3ccnc3)c(Nc3ccc(OC)cc3)c2c1] | (1H-imidazol-1-yl)methyl 4-(4-methoxyphenylamino)-6-(methylcarbamoyl)-quinoline-3-carboxylate. |
| II-2 | 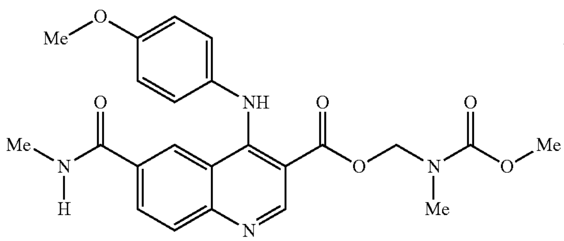 [SMILES: CNC(=O)c1ccc2ncc(C(=O)OCN(C)C(=O)OC)c(Nc3ccc(OC)cc3)c2c1] | (Methoxycarbonyl(methyl)amino)methyl 4-(4-methoxyphenyl-amino)-6-(methylcarbamoyl)-quinoline-3-carboxylate |
| II-3 | 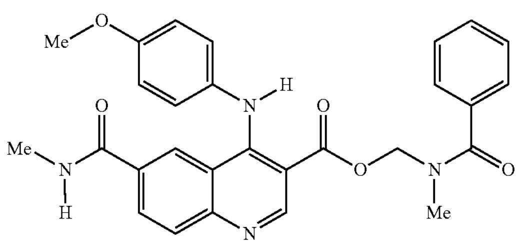 [SMILES: CNC(=O)c1ccc2ncc(C(=O)OCN(C)C(=O)c3ccccc3)c(Nc3ccc(OC)cc3)c2c1] | (N-methylbenzamido)methyl 4-(4-methoxyphenyl-amino)-6-(methyl-carbamoyl)-quinoline-3-carboxylate |
| II-4 | 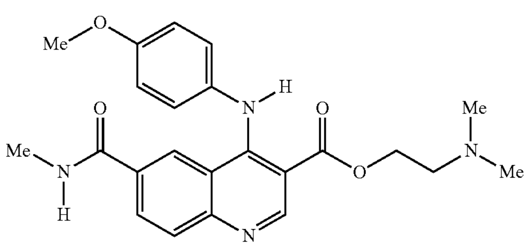 [SMILES: CNC(=O)c1ccc2ncc(C(=O)OCCN(C)C)c(Nc3ccc(OC)cc3)c2c1] | 2-(dimethylamino)-ethyl 4-(4-methoxyphenyl-amino)-6-(methylcarbamoyl)-quinoline-3-carboxylate |
| II-5 | 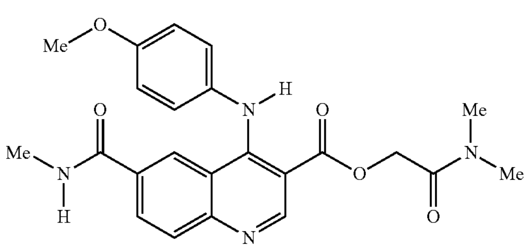 [SMILES: CNC(=O)c1ccc2ncc(C(=O)OCC(=O)N(C)C)c(Nc3ccc(OC)cc3)c2c1] | 2-(dimethylamino)-2-oxoethyl-4-(4-methoxyphenyl-amino)-6-(methyl-carbamoyl)quinoline-3-carboxylate. |
| II-6 | 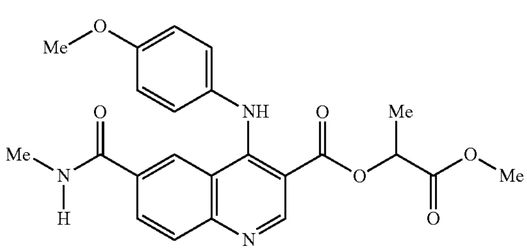 [SMILES: CNC(=O)c1ccc2ncc(C(=O)OC(C)C(=O)OC)c(Nc3ccc(OC)cc3)c2c1] | (2-Methoxy-1-methyl-2-oxo-ethyl) 4-[(4-methoxyphenyl)-amino]-6-(methylcarbamoyl)quinoline-3-carboxylate |

| Comp. No. | Chemical Structure | Chemical Name |
|---|---|---|
| II-7 | 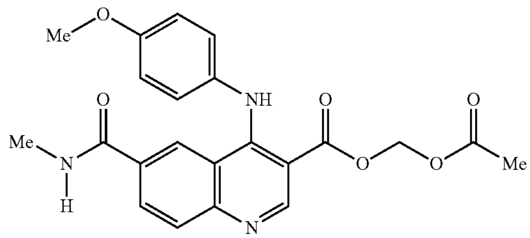 [SMILES: CNC(=O)c1ccc2ncc(C(=O)OCOC(C)=O)c(Nc3ccc(OC)cc3)c2c1] | Acetoxymethyl 4-[(4-methoxyphenyl)amino]-6-(methylcarbamoyl)quinoline-3-carboxylate |
| II-8 | 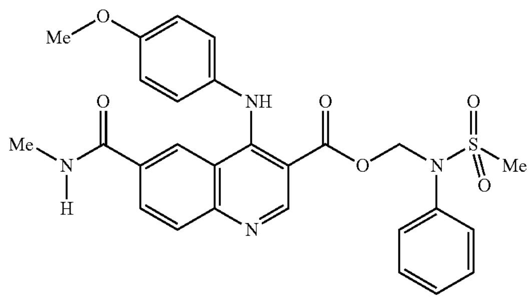 [SMILES: CNC(=O)c1ccc2ncc(C(=O)OCN(c3ccccc3)S(C)(=O)=O)c(Nc3ccc(OC)cc3)c2c1] | (Methylsulfonyl(phenyl)amino)methyl 4-[(4-methoxyphenyl)-amino]-6-(methylcarbamoyl)-quinoline-3-carboxylate |
| II-9 | 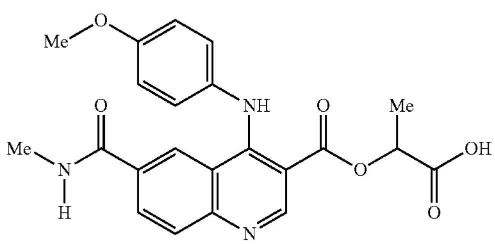 [SMILES: CNC(=O)c1ccc2ncc(C(=O)OC(C)C(=O)O)c(Nc3ccc(OC)cc3)c2c1] | 2-[4-[(4-Methoxyphenyl)-amino]-6-(methylcarbamoyl)quinoline-3-carbonyl]-oxypropanoic acid |
| II-10 | 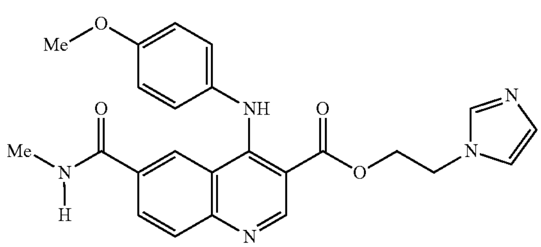 [SMILES: CNC(=O)c1ccc2ncc(C(=O)OCCn3ccnc3)c(Nc3ccc(OC)cc3)c2c1] | 2-Imidazol-1-ylethyl 4-[(4-methoxyphenyl)-amino]-6-(methylcarbamoyl)-quinoline-3-carboxylate |
| II-11 | 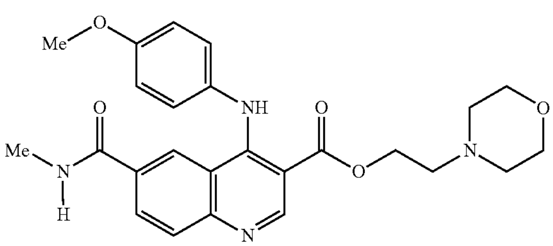 [SMILES: CNC(=O)c1ccc2ncc(C(=O)OCCN3CCOCC3)c(Nc3ccc(OC)cc3)c2c1] | 2-Morpholinoethyl 4-[(4-methoxyphenyl)-amino]-6-(methylcarbamoyl)-quinoline-3-carboxylate |
| II-12 | 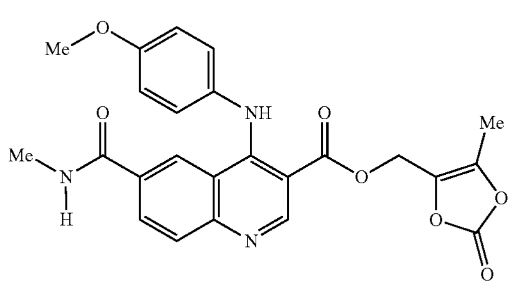 [SMILES: CNC(=O)c1ccc2ncc(C(=O)OCc3oc(=O)oc3C)c(Nc3ccc(OC)cc3)c2c1] | (5-Methyl-2-oxo-1,3-dioxol-4-yl)methyl 4-[(4-methoxyphenyl)-amino]-6-(methylcarbamoyl)-quinoline-3-carboxylate |

-continued

| Comp. No. | Chemical Structure | Chemical Name |
|---|---|---|
| II-13 | 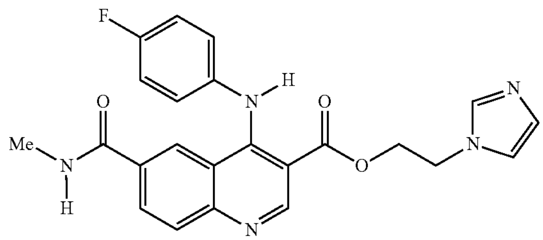 [SMILES: CNC(=O)c1ccc2ncc(C(=O)OCCn3ccnc3)c(Nc3ccc(F)cc3)c2c1] | 4-(4-Fluoro-phenylamino)-6-methylcarbamoyl-quinoline-3-carboxylic acid-2-imidazol-1-yl-ethylester |
| II-14 | 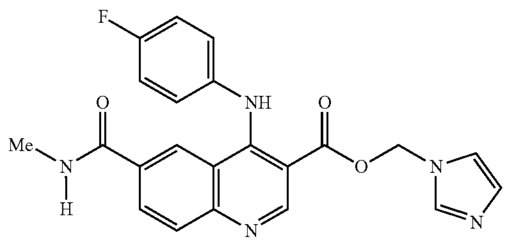 [SMILES: CNC(=O)c1ccc2ncc(C(=O)OCn3ccnc3)c(Nc3ccc(F)cc3)c2c1] | 4-(4-Fluoro-phenylamino)-6-methylcarbamoyl-quinoline-3-carboxylic acid imidazol-1-yl-methylester |
| II-15 | 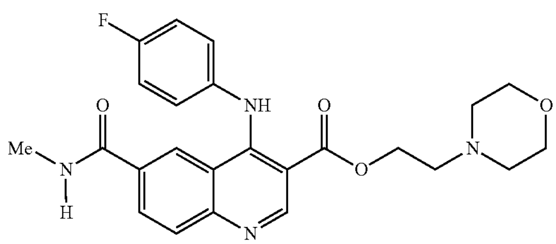 [SMILES: CNC(=O)c1ccc2ncc(C(=O)OCCN3CCOCC3)c(Nc3ccc(F)cc3)c2c1] | 2-Morpholinoethyl 4-[(4-fluorophenyl)amino]-6-(methylcarbamoyl)quinoline-3-carboxylate |

An example of a compound Formula III useful in accordance with the present invention is a compound selected from any one of the following compounds Nos. III-1 to III-9:

| Comp. No. | Chemical Structure | Chemical Name |
|---|---|---|
| III-1 | 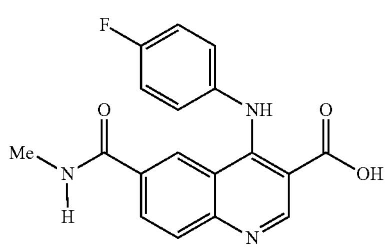 [SMILES: CNC(=O)c1ccc2ncc(C(=O)O)c(Nc3ccc(Cl)cc3)c2c1] | 4-(4-fluorophenylamino)-6-(methylcarbamoyl)quinoline-3-carboxylic acid |
| III-2 | 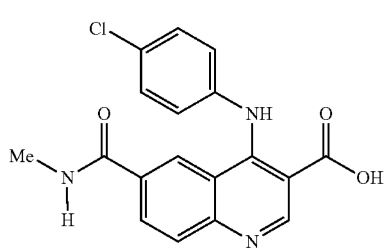 | 4-(4-chlorophenylamino)-6-(methylcarbamoyl)quinoline-3-carboxylic acid |

-continued

| Comp. No. | Chemical Structure | Chemical Name |
|---|---|---|
| III-3 | 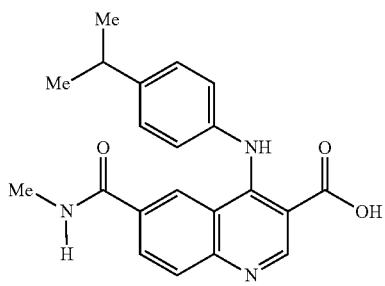 [SMILES: CNC(=O)c1ccc2ncc(C(=O)O)c(Nc3ccc(C(C)C)cc3)c2c1] | 4-[(4-Isopropylphenyl)amino]-6-(methylcarbamoyl)quinoline-3-carboxylic acid |
| III-4 | 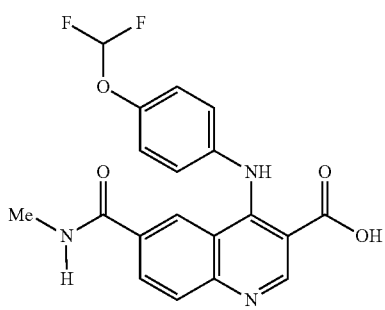 [SMILES: CNC(=O)c1ccc2ncc(C(=O)O)c(Nc3ccc(OC(F)F)cc3)c2c1] | 4-[[4 (Difluoromethoxy)phenyl]amino]-6-(methylcarbamoyl)quinoline-3-carboxylic acid |
| III-5 | 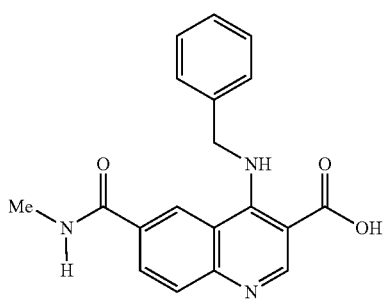 [SMILES: CNC(=O)c1ccc2ncc(C(=O)O)c(NCc3ccccc3)c2c1] | 4-Benzylamino-6-methylcarbamoyl-quinoline-3-carboxylic acid |
| III-6 | 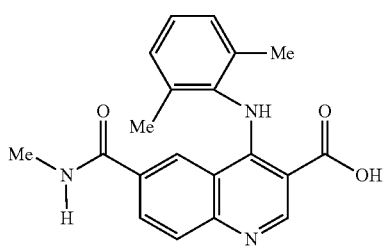 [SMILES: CNC(=O)c1ccc2ncc(C(=O)O)c(Nc3c(C)cccc3C)c2c1] | 4-(2,6-Dimethyl-phenylamino)-6-methylcarbamoyl-quinoline-3-carboxylic acid |
| III-7 | 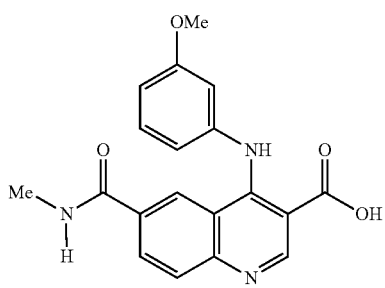 [SMILES: CNC(=O)c1ccc2ncc(C(=O)O)c(Nc3cccc(OC)c3)c2c1] | 4-(3-Methoxy-phenylamino)-6-methylcarbamoyl-quinoline-3-carboxylic acid |

| Comp. No. | Chemical Structure | Chemical Name |
|---|---|---|
| III-8 | 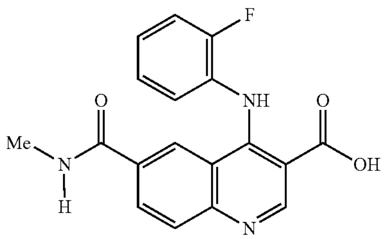 [SMILES: CNC(=O)c1ccc2ncc(C(=O)O)c(Nc3ccccc3F)c2c1] | 4-(2-Fluoro-phenylamino)-6-methylcarbamoylquinoline-3-carboxylic acid |
| III-9 | 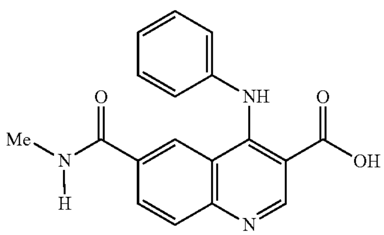 [SMILES: CNC(=O)c1ccc2ncc(C(=O)O)c(Nc3ccccc3)c2c1] | 6-Methylcarbamoyl-4-phenylamino-quinoline-3-carboxylic acid |

It should be noted, however, that the compounds I-2 and I-4 are also comprised within the scope of Formula III, as defined herein, while compounds III-1 to III-9 are also comprised within the scope of Formula I, as defined herein.

Compounds of Formula I useful in accordance with the present invention may be prepared as described in WO 2009/063070.

Compounds of Formula II useful in accordance with the present invention may be prepared as described in WO 2010/133669.

Compounds of Formula III useful in accordance with the present invention may be prepared as described in WO 2010/133672.

An aspect of the present invention is a compound according to Formula I, II or III above, for use in the treatment of a fibrotic disease such as a fibrotic disease affecting the lung, liver, kidney, skin, epidermis, endodermis, muscle, tendon, cartilage, heart, stomach, large intestine, small intestine, colon, uterus, nervous system, testis, adrenal gland, artery, vein, biliary tract, or eye.

Examples of fibrotic diseases where a compound of formula I, II, or III as disclosed herein may be useful, are:

Hepatic fibrosis: liver fibrosis; liver cirrhosis; reperfusion injury after hepatic transplantation; necrotizing hepatitis.

Renal fibrosis: glomerulonephritis; IgA nephropathy; reperfusion injury after kidney transplantation; chronic renal allograft dysfunction; amyloidosis; diabetic nephropathy; mesangio proliferative glomerulonephritis; nephrosclerosis.

Lung fibrosis: Interstitial Lung Disease (ILD) such as idiopathic pulmonary fibrosis; cystic fibrosis (CF); interstitial pulmonary fibrosis; drug-induced fibrosis; sarcoidosis; diffuse alveolar damage disease; pulmonary hypertension; chronic obstructive pulmonary disease; respiratory distress syndrome; lymphangioleiomyomatosis.

Skin fibrosis: scleroderma; keloid; hypertrophic scar; dermatofibroma; chronic wounds; psoriasis; Dupuytren's contracture; pemphigoid; burn.

Stomach and intestinal fibrosis: abnormal intestinal motility; hypertrophic pyloric stenosis; Hirschsprung's disease; megacolon of piebaldism; idiopathic obstruction; collagenous colitis; villous atrophy and crypt hyperplasia; polyp formation; fibrosis of Crohn's disease; gastric ulcer.

Eye fibrosis: acute and fibrotic sympathetic ophthalmia; Grave's disease; fibrosis after glaucoma surgery; fibrosis after cataract surgery; anterior capsular cataract; corneal scarring; pemphigoid; diabetic microaneurism; capsule opacification; elastoid degeneration of the conjunctiva resulting in pingueculae and pterygia (fibrovascular growths on the surface of the cornea); visual loss secondary to pinguecula; filtering bleb survival disease; macular degeneration; or retinal and vitreal retinopathy such as proliferative diabetic retinopathy and proliferative vitreoretinopathy (PVR).

Other fibrosis: endometriosis; uterine fibroid; fibromyalgia; systemic sclerosis; artherosclerosis; restenosis; chronic myeloproliferative disorders; fibrodysplasia ossificans progressiva; myelodysplasia; osteoporosis; myelofibrosis; osteosclerosis; rheumatoid pannus formation in rheumatoid arthritis and osteoarthritis; peritoneal fibrosis; myocardial fibrosis; pancreatic fibrosis; chronic pancreatitis; glial scar tissue formation in HIV; associated cognitive motor disease and spongiform encephalopathy; or gingival hypertrophy secondary to drugs and fibrocystic disease.

Ocular diseases which are connected with choroidal neovascularization and possibly followed by fibrosis:ocular histoplasmosis syndrome; high myopia; angoid streaks; choroidal rupture; optic disc drusen; optic pits; acute posterior multifocal placoid pigment epitheliopathy; serpiginous choroiditis; Harada's disease; Stargard's disease; toxoplasmosis; sarcoidosis; central serous retinopathy; congenital rubella; coloboma; morning glory syndrome; choroidal hemangioma; choroidal melanoma; choroidal nevus; choroidal osteoma; toxocariasis; branch retinal vein occlusion; central retinal vein occlusion; parafoveal telangiectasis; retinitis pigmentosa; Best's disease; adult foveal macular dystrophy; problems after photocoagulation or retinal vascular diseases such as e.g., hypertensive retinopathy; diabetic retinopathy; sickle cell retinopathy; retinopathy of prematurity; background retinopathy; other eye diseases connected with neovascularization and/or integrin mediated interactions such as, e.g., proliferative vitreoretinopathy; proliferative diabetic retinopathy: Behçet's disease, cavernous hemangioma of the retina: choroidal rupture: retinal telangiectasia; cystoid maculopathy; Eale's disease; idiopathic central serous choroidopathy; iris neovascularization; malignant choroidal melanoma; preretinal macula fibrosis; ocular histoplasmosis; retinal capillary hemangiomaretinal tumors; tumors of the iris and ciliary body; diseases with pathological corneal neovascularization; pterygia.

Still another aspect of the present invention is a compound according to Formula I, II or III as disclosed herein, for use in the treatment of Lymphangioleiomyomatosis (LAM).

It is known that fibrosis and inflammation may be the cause of failure of surgical therapy. Still another aspect of the present invention therefore is a compound according to Formula I, II or III as disclosed herein for use in the treatment of fibrosis, or a fibrotic or inflammatory disorder, in connection with surgery. Examples of surgical interventions which may profit from the concomitant treatment (before or after the surgical intervention or both before and after) administration of a compound of the invention are: filtration surgery (trabeculectomy), laser trabeculoplasty, laser cyclophotocoagulation (cycloablation) for end-stage glaucoma, surgery for acute closed-angle glaucoma, drainage implants (tube shunts), deep sclerectomy, ex-press mini-shunt, trabectome surgery, iridotomy and iridectomy, canaloplasty and viscocanolostomy. and goniotomy.

Thus, an aspect of the present invention is a compound of formula I, II or III, as disclosed herein, for use in the treatment of fibrosis in connection with a surgical intervention selected from filtration surgery (trabeculectomy), laser trabeculoplasty, laser cyclophotocoagulation (cycloablation) for end-stage glaucoma, surgery for acute closed-angle glaucoma, drainage implants (tube shunts), deep sclerectomy, ex-press mini-shunt, trabectome surgery, iridotomy and iridectomy, canaloplasty and viscocanolostomy. and goniotomy.

An aspect of the present invention is the use of a compound of formula I, II or III as disclosed herein, for the manufacture of a medicament for use in the treatment of fibrosis.

Yet another aspect of the invention is a method for the treatment of fibrosis, whereby a therapeutically effective amount of a compound of formula I, II or III, is administered to a patient in need of such treatment.

The wording "fibrosis" is herein defined as a fibroproliferative disease. Generally, fibrotic disorders are characterized by inappropriate overproliferation or transdifferentiation of non-cancerous mostly fibroblastic cells.

The wording "fibrosis-related disease" is herein defined as a disease or condition which may occur as a result of fibrosis or which is associated with or worsened by fibrosis. Without being limiting, examples of such fibrosis-related diseases are solid cancers, chronic inflammation, infections and psoriasis. A fibrosis-related disease also may be a condition occurring as a consequence of the development of fibrosis following a surgical intervention.

The wording "Interstitial lung disease (ILD)" includes a wide range of distinct disorders in which pulmonary inflammation and fibrosis are the final common pathways of pathology. There are more than 150 causes of ILD, including sarcoidosis, silicosis, drug reactions, infections and collagen vascular diseases, such as rheumatoid arthritis and systemic sclerosis (also known as scleroderma).

The wording "Idiopathic pulmonary fibrosis" is the most common type of Interstitial lung disease (ILD) and has no known cause.

The wording "Liver cirrhosis" has similar causes to Interstitial lung disease (ILD), with viral hepatitis, schistosomiasis and chronic alcoholism being the main causes worldwide.

The wording "Fibrotic Kidney disease" may be caused by diabetes which may damage and scar the kidneys, which leads to a progressive loss of function.

Diseases of the cornea can be acquired secondary to infection (e.g. herpetic keratitis) or inflammation (e.g. pterygia). Elastoid degeneration of the conjunctiva, resulting in pingueculae and pterygia (fibrovascular growths on the surface of the cornea). The final common events in all of these diseases are often inflammatory changes associated with neovascularization, tissue edema, and, ultimately, fibrosis of the corneal stroma, which leads to opacification and decreased vision (Fini, M. E. 1999. Prog. Retin. Eye Res. 18:529-551.)

The wording "Scarring associated with trauma" includes but is not limited to surgical complications with scar tissue that may form between internal organs, causing contracture, pain and, in some cases, infertility, and which may be severe when persistent. Yet another example is fibrosis due to burns.

The wording "Chemotherapeutic drug-induced fibrosis" includes but is not limited to fibrosis which is caused by certain pharmaceuticals, such as drug-induced lung disease, or eye fibrosis which may be caused by anti-VEGF monoclonal antibody treatment such as bevacizumab or ranibizumab (Hwang J C et al. Ophthalmic Surg Lasers Imaging. 2011 January-February; 42(1):6-11; Mariani A et al. Graefes Arch Clin Exp Ophthalmol. 2011 November; 249(11); Muriel M A et al. Arch Soc Esp Oftalmol. 2011 August; 86(8):254-9; Rosenfeld P J et al. Ophthalmology. 2011 March; 118(3):523-30; Ramasubramanian A et al. Br J Ophthalmol. *Br J Ophthalmol bjophthalmol*-2011-300141*Published Online First:* 7 Jun. 2011.

The wording "Radiation-induced fibrosis (RIF)" includes but is not limited to fibrosis which is a serious and common complication of radiation therapy that may cause chronic pain, neuropathy, limited movement of joints, and swelling of the lymph nodes. It occurs most often in breast, head, neck, and connective tissues. RIF may develop from 4-6 months to 1-2 years following exposure to radiation therapy, and it becomes more severe over time. Risk factors for developing RIF include high radiation dose, large volumes of tissue exposed to radiation, and radiation combined with surgery, chemotherapy, or both.

The wording "Lymphangioleiomyomatosis (LAM)" is a rare lung disease that results in a proliferation of disorderly smooth muscle growth (leiomyoma) throughout the lungs, in the bronchioles, alveolar septa, perivascular spaces, and lymphatics, resulting in the obstruction of small airways (leading to pulmonary cyst formation and pneumothorax) and lymphatics (leading to chylous pleural effusion). LAM occurs in a sporadic form, which only affects females, who are usually of childbearing age. LAM also occurs in patients who have tuberous sclerosis.

The wording "Subretinal fibrosis" is herein defined as Age Related macular Degeneration (ARMD). The leading cause of vision loss in Americans over the age of 65 is ARMD; 12-15 million Americans over the age of 65 have this disease and 10%-15% of them will lose central vision as a direct effect of choroidal (subretinal) neovascularization and fibrosis.

Yet another aspect of the present invention is a pharmaceutical combination, comprising
(i) a compound of formula I

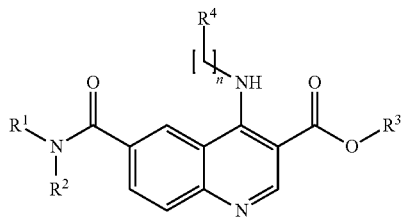

wherein
n=0, 1 or 2;
$R^1$ and $R^2$ are each independently selected from hydrogen; saturated or unsaturated, branched or unbranched $C_{1-10}$ alkyl or $C_{3-12}$ cycloalkyl; and substituted or non-substituted phenyl or benzyl;
$R^3$ is hydrogen; or saturated or unsaturated, branched or unbranched $C_{1-10}$ alkyl or $C_{3-12}$ cycloalkyl;
$R^4$ is substituted or non-substituted $C_6$-$C_{10}$ aryl or $C_5$-$C_9$ heteroaryl wherein the heteroatoms independently are selected from N, O and S; or substituted or non-substituted mono- or bicyclic $C_{3-12}$ cycloalkyl or $C_5$-$C_9$ heterocyclyl wherein the heteroatoms are independently selected from N, O and S;
or a pharmaceutically acceptable salt thereof; and
(ii) a drug that suppresses the immune system or which has other beneficial effects targeting processes that precede fibrosis;
for simultaneous, separate or sequential administration.

Yet another aspect of the present invention is a pharmaceutical combination, comprising
(i) a compound of formula II

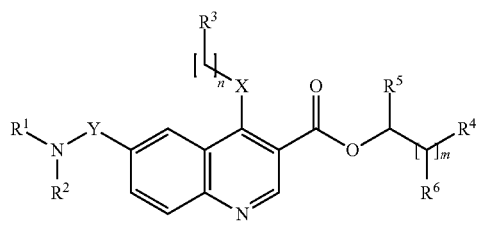

wherein:
n is 0 (zero) or 1;
m is 0 (zero), 1 or 2;
$R^1$ and $R^2$ are each independently selected from hydrogen; branched or unbranched $C_1$-$C_8$ alkyl, $C_2$-$C_8$ alkenyl or $C_2$-$C_8$ alkynyl; monocyclic or bicyclic, saturated or unsaturated $C_3$-$C_8$ carbocyclyl; and monocyclic or bicyclic, saturated or unsaturated
$C_3$-$C_7$ heterocyclyl wherein each heteroatom is independently selected from N, O and S;
said alkyl, alkenyl, alkynyl, carbocyclyl or heterocyclyl optionally being substituted with 1, 2 or 3 groups $R^a$;
$R^3$ is selected from monocyclic or bicyclic $C_6$-$C_{10}$ aryl; and monocyclic or bicyclic $C_3$-$C_9$ heteroaryl or heterocyclyl, wherein in said heteroaryl and heterocyclyl each heteroatom is independently selected from N, O and S; said aryl, heteroaryl or heterocyclyl optionally being substituted with 1, 2, 3, 4 or 5 groups $R^b$;

$R^4$ is selected from $—OC(O)R^7$; $—C(O)OR^7$; $—NR^7R^8$; $—C(O)NR^7R^8$; monocyclic or bicyclic $C_3$-$C_9$ heteroaryl; and monocyclic or bicyclic, saturated or unsaturated $C_5$-$C_9$ heterocyclyl, wherein said heteroaryl and heterocyclyl optionally contains an oxo group in the ring, and wherein in said heteroaryl and heterocyclyl each heteroatom independently is selected from N, O and S; said heteroaryl and heterocyclyl optionally being substituted with 1, 2 or 3 groups $R^a$;
$R^5$ and $R^6$ are each independently selected from hydrogen; and branched or unbranched $C_1$-$C_4$ alkyl, $C_2$-$C_4$ alkenyl or $C_2$-$C_4$ alkynyl; said alkyl, alkenyl and alkynyl optionally being substituted with 1, 2, or 3 groups independently selected from fluorine and chlorine;
$R^7$ is selected from hydrogen; and branched or unbranched $C_1$-$C_4$ alkyl, $C_2$-$C_4$ alkenyl or $C_2$-$C_4$ alkynyl; and phenyl; said alkyl, alkenyl, alkynyl and phenyl optionally being substituted with 1, 2, or 3 groups independently selected from fluorine and chlorine;
$R^8$ is selected from hydrogen; branched or unbranched $C_1$-$C_4$ alkyl, $C_2$-$C_4$ alkenyl or $C_2$-$C_4$ alkynyl; monocyclic or bicyclic $C_6$-$C_{10}$ aryl; $—S(O)_2R^9$; $—C(O)OR^9$; and $—C(O)R^{10}$; said alkyl, alkenyl, alkynyl or aryl optionally being substituted with 1, 2, or 3 halogen(s);
$R^9$ is selected from hydrogen and branched or unbranched $C_1$-$C_4$ alkyl, $C_2$-$C_4$ alkenyl or $C_2$-$C_4$ alkynyl; said alkyl, alkenyl and alkynyl optionally being substituted with 1, 2, or 3 groups independently selected from fluorine and chlorine;
$R^{10}$ is selected from hydrogen; branched or unbranched $C_1$-$C_4$ alkyl, $C_2$-$C_4$ alkenyl or $C_2$-$C_4$ alkynyl; and $C_6$ aryl; said aryl optionally being substituted with 1, 2 or 3 groups $R^a$;
and said alkyl, alkenyl and alkynyl optionally being substituted with 1, 2, or 3 groups independently selected from fluorine and chlorine;
Y is selected from $—C(O)—$; $—S(O)—$; and $—S(O)_2—$;
X is selected from $—NR^c—$; $—O—$; and $—S—$;
each $R^a$ is independently selected from halogen; hydroxy; carbonyl; methoxy; halomethoxy; dihalomethoxy; and trihalomethoxy;
each $R^b$ is independently selected from halogen; carboxy; hydroxy; cyano; $C_1$-$C_4$ alkyl; $C_2$-$C_4$ alkenyl; $C_2$-$C_4$ alkynyl; $C_1$-$C_4$ alkyloxy; $C_2$-$C_4$ alkenyloxy; $C_2$-$C_4$ alkynyloxy; $C_1$-$C_4$ alkylthio; $C_2$-$C_4$ alkenylthio; $C_2$-$C_4$ alkynylthio; $C_1$-$C_4$ alkyl; $C_2$-$C_4$ alkenyl or $C_2$-$C_4$ alkynyl secondary or tertiary amino; $C_1$-$C_4$ alkyl, $C_2$-$C_4$ alkenyl or $C_2$-$C_4$ alkynyl secondary or tertiary amido; $C_1$-$C_4$ alkyl, $C_2$-$C_4$ alkenyl or $C_2$-$C_4$ alkynyl carbonyl; $C_1$-$C_4$ alkyl, $C_2$-$C_4$ alkenyl or $C_2$-$C_4$ alkynyl sulfonyl; $C_1$-$C_4$ alkyl, $C_2$-$C_4$ alkenyl or $C_2$-$C_4$ alkynyl sulfonyloxy;
$C_1$-$C_4$ alkyl, $C_2$-$C_4$ alkenyl or $C_2$-$C_4$ alkynyl secondary or tertiary sulfonamido; $C_1$-$C_4$ alkyl, $C_2$-$C_4$ alkenyl or $C_2$-$C_4$ alkynyl silyl; and $C_1$-$C_4$ alkyloxy, $C_2$-$C_4$ alkenyloxy, or $C_2$-$C_4$ alkynyloxy carbonyl; wherein any alkyl, alkenyl and alkynyl moiety optionally is substituted with 1, 2 or 3 groups independently selected from halogen, hydroxy, methoxy, halomethoxy, dihalomethoxy and trihalomethoxy; and
$R^c$ is selected from hydrogen; and branched or unbranched $C_1$-$C_4$ alkyl, $C_2$-$C_4$ alkenyl or $C_2$-$C_4$ alkynyl;
wherein any $C_p$ alkyl, alkynyl or alkenyl group having a number p≥4 of carbon atoms optionally includes a $C_q$ carbocyclic portion of q of carbon atoms, whereby 3≤q<p;
or a pharmaceutically acceptable salt thereof; and
(ii) a drug that suppresses the immune system or which has other beneficial effects targeting processes that precede fibrosis;
for simultaneous, separate or sequential administration.

Yet another aspect of the present invention is a pharmaceutical combination, comprising
(i) a compound of formula III

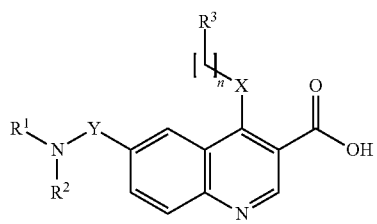

wherein
n is 0 (zero) or 1;

R$^1$ and R$^2$ are each independently selected from hydrogen; branched or unbranched C$_1$-C$_8$ alkyl, C$_2$-C$_8$ alkenyl, or C$_2$-C$_8$ alkynyl; monocyclic or bicyclic, saturated or unsaturated C$_3$-C$_8$ carbocyclyl; and monocyclic or bicyclic, saturated or unsaturated
C$_3$-C$_7$ heterocyclyl wherein the heteroatoms are independently selected from N, O and S; said alkyl, alkenyl, alkynyl, carbocyclyl or heterocyclyl optionally being substituted with 1, 2, or 3 groups R$^a$;

R$^3$ is selected from monocyclic or bicyclic C$_6$-C$_{10}$ aryl; and monocyclic or bicyclic C$_5$-C$_9$ heteroaryl, wherein the heteroatoms independently are selected from N, O and S; said aryl or heteroaryl optionally being substituted with 1, 2, 3, 4 or 5 groups R$^b$;

Y is selected from —C(O)—; —S(O)—; and —S(O)$_2$—;
X is selected from —NR$^c$—; —O—; and —S—;

each R$^a$ is independently selected from halogen; hydroxy; carbonyl; methoxy; halomethoxy; dihalomethoxy; and trihalomethoxy;

each R$^b$ is independently selected from halogen, branched or unbranched C$_1$-C$_4$ alkyl, C$_2$-C$_4$ alkenyl or C$_2$-C$_4$ alkynyl; branched or unbranched C$_1$-C$_4$alkyloxy, C$_2$-C$_4$alkenyloxy or C$_2$-C$_4$ alkynyloxy; branched or unbranched C$_1$-C$_4$ alkylthio, C$_2$-C$_4$alkenylthio or C$_2$-C$_4$alkynylthio; said alkyl, alkenyl, alkynyl, alkyloxy, alkenyloxy alkynyloxy, alkylthio, alkenylthio or alkynylthio group optionally being substituted with 1, 2 or 3 halogens;

R$^c$ is selected from hydrogen and branched or unbranched C$_1$-C$_4$ alkyl, C$_2$-C$_4$ alkenyl or C$_2$-C$_4$ alkynyl;

or a pharmaceutically acceptable salt thereof; and
(ii) a drug that suppresses the immune system or which has other beneficial effects targeting processes that precede fibrosis;
for simultaneous, separate or sequential administration.

Examples of a drug that suppresses the immune system or which has other beneficial effects targeting processes that precede fibrosis and which may be useful in combination with a compound of formula I, II or III as herein described, are a corticosteroid such as prednisone; a cytostatic such as methotrexate; cyclosporine; an antibiotic such as azithromycin; a mucolytical such as acetylcysteine; an anti-rheumathic drug such as sulfasalazine; an anti-VEGF drug such as ranibizumab (Lucentis®), Pegaptanib (Macugen®), Bevacizumab (Avastin®) or VEGF-trap (EYLEA®).

The wording "simultaneous administration" is herein defined as the administration to a patient of a compound of formula I, II or III, administered together with a drug that suppresses the immune system or which has other beneficial effects targeting processes that precede fibrosis.

In one aspect of the invention, simultaneous administration may be as a fixed-dose combination such as a pharmaceutical formulation comprising a compound of formula I, II or III, and a drug that suppresses the immune system or which has other beneficial effects targeting processes that precede fibrosis in admixture with a pharmaceutically acceptable adjuvant and/or carrier.

In yet another aspect of the invention, a drug that suppresses the immune system or which has other beneficial effects targeting processes that precede fibrosis, may be administered to a subject suffering from fibrosis, followed by the administration of a compound of formula I, II or III as herein described.

All substituents of a compound of formula I, II or III as described throughout the present specification and claims, are defined in accordance with the definitions for each such substituent as disclosed in WO 2009/063070, WO 2010/133669 and WO 2010/133672.

Thus, for example, in a substituted entity any substituent may be selected from saturated or unsaturated, branched, unbranched or cyclic lower alkyl; hydroxyl, amine, sulfide, silyl, halogen, cyano, carboxy, sulfonic acid, lower alkoxy, lower alkyl secondary or tertiary amine, lower alkyl amide, lower alkyl ether, lower alkyl ketone, lower alkyl sulfide, lower alkyl carboxylic acid ester, lower alkyl sulfonic acid ester, lower alkyl sulfone, lower alkyl sulfoxide, lower alkyl sulfonamide, lower alkyl alcohol, lower alkyl acetyl, lower dialkyl disulfide. As used herein, the term "lower alkyl" refers to a C1-C6 alkyl, e.g. a C1-C4 alkyl, such as a C1-C3 alkyl.

Pharmaceutical Formulations

For clinical use, a compound of formula I, II or III as herein described for use in fibrosis, may be administered as a pharmaceutical formulation for oral administration.

In one aspect of the invention, a compound of formula I, II or III as herein described for use in fibrosis, may be administered locally to the eye, such as by intraocular or periocular injection, or in the form of a local implant, or topically in the form of eye drops or in the form of an ointment.

Examples of intraocular injections are intravitreal, intracameral or sub-retinal injections. Examples of periocular injections are subconjunctival, para/retro bulbar, juxtascleral, and sub-tenual.

In the case of local implants, specialized sustained-release devices may be administered the intraocular or periocular route, to enable a constant, slow release of the drug compound to the eye (Robinson, 2002, Exp. Eye Res, 74, 309; Geroski, 2000, 41, 961). Other sustained-release systems are microsheres, liposomes, nanoparticles or other polymer matrices (Bourlais, 1998, Prog. Retin Eye Res. 17, 33).

In yet another aspect of the invention, a compound of formula I, II or III as herein described, may be administered by the intravitreal (IVT) administration route.

The term "therapeutically effective amount" as used herein refers to an amount of a therapeutic agent, such as a compound of any one of Formulas I, II or III as disclosed herein. The amount is the amount sufficient to exhibit a therapeutic or preventative or ameliorative effect. The effect may include, for example, treatment or prevention of the conditions listed herein. The precise effective amount for a subject will depend upon the subject's size and general condition, the nature and extent of the condition being treated, recommendations of the treating physician, and the therapeutics or combination of therapeutics selected for administration. In the case of oral administration the dosage may vary from about 0.01 mg to about 1000 mg per day of a compound of any one of Formulas I, II or III or a pharmaceutically acceptable salt thereof.

EXAMPLES

Preparation of 4-[(4-Methoxyphenyl)amino]-6-(methylcarbamoyl)quinoline-3-carboxylic acid (Compound I-4 above) hydrochloride The hydrochloride salt of the compound 4-[(4-methoxyphenyl)amino]-6-(methylcarbamoyl)quinoline-3-carboxylic acid (compound I-4 above, prepared as disclosed in Example 4 of WO 2009/063070) was obtained from Ethyl 6-(methylcarbamoyl)-4-[(4-methoxylphenyl)amino]quinoline-3-carboxylate hydrochloride which was obtained as described in Example 3 of WO 2009/063070.

To a solution of ethyl 6-(methylcarbamoyl)-4-[(4-methoxylphenyl)amino]quinoline-3-carboxylate hydrochloride (100.0 g, 0.2636 mol, 1.0 equiv.) in THF (4.0 L) was added aqueous 1N NaOH solution (1.320 L, 52.8 g, 1.3 mol, 5.0 equiv.) at room temperature. The clear red solution was heated to 50° C. with constant stirring for 3 h. The reaction was monitored with TLC (10% MeOH in CHCl3, Rf: 0.1). The reaction mixture was allowed to attain room temperature and diluted with $H_2O$ (5.0 L). Two layers were formed. The suspension was evaporated under reduced pressure to remove major portion of THF. The remaining red coloured aqueous portion was washed with MTBE (2×2.5 L). The pale yellow aqueous layer was cooled to 0° C. (ice-batch) and acidified with aqueous 1N HCl (2.0 L) with vigorous stirring until the pH of the reaction mixture reaches 1. During this time yellow solid precipitated out. After complete addition, the mixture was stirred vigorously at room temperature for 16 h. The yellow solid was filtered through a Buchner funnel and washed with $H_2O$ (2×500 mL) followed by MTBE (500 mL). The yellow solid was freeze dried for 45 h to provide the final compound, I-4 (86.0 g, 93%) as a free-flowing yellow powder.

MW 351.37 (free base), MW 387.83 hydrochloride. $^1$H NMR (300 MHz, D6-DMSO) 9.05 (s, 1H, aromatic), 8.70 (bm, 2H, aromatic and NH), 8.20 (d, 1H, aromatic), 8.00 (d, 1H, aromatic), 7.4 (d, 2H, aromatic), 7.00 (d, 2H, aromatic), 3.88 (s, 1H, —OCH$_3$), 2.7 (s, 3H, —NCH$_3$); LC-MS (m/z) 352.0 (M+1).

Biological Evaluation
Bleomycin-induced Lung Fibrosis Mouse Model

Pulmonary fibrosis is a common response to various insults to the lung and is the end-point of a numerous and heterogenous group of disorders known as interstitial lung disease (ILD), characterized by chronic inflammation and progressive fibrosis of the pulmonary interstitium. Intrathecal instillation of the anti-tumour agent bleomycin (BLM) is the most commonly used animal model for pulmonary fibrosis.

Thirty male CD-1 mice weighing 27.5±0.4 g were used in this study (obtained from Harlan Nossan, Milan, Italy), and were allowed access to food and water ad libitum. The mice were kept in laminar flow rooms at constant temperature and humidity with 3 animals in each cage. The temperature of the room was controlled between 20-26° C. and the humidity of the room was controlled between 40-70%.

Mice received a single intra-tracheal instillation of saline (0.9%), or saline containing bleomycin sulfate (BLM, 0.1 IU per mouse) in a volume of 100 µl. Mice were then sacrificed after 7 days by pentobarbitone overdose.

Animals were randomized into three experimental groups of 10 animals in each group, and were treated with either hydroxypropyl methyl cellulose (HPMC) (0.5%)/HPbetaCyclodextrin (20%) as a 5 ml/kg s.c. injection 30 min after intra-tracheal instillation of BLM and every 12 h thereafter until completion of the study, or with the compound I-4×HCl (4-[(4-Methoxyphenyl)amino]-6-(methylcarbamoyl)quinoline-3-carboxylic acid hydrochloride) at 30 mg/kg as a s.c. injection 30 min after intra-tracheal instillation of BLM and every 12 h thereafter until completion of the study.

TABLE 1

Experimental Design

| Group | Treatment | 0 min after BLM Dose [mg/kg] | 0 min after BLM Dose Volume [ml/kg] | Every 12 h after BLM Dose [mg/kg] | Every 12 h after BLM Dose Volume [ml/kg] |
| --- | --- | --- | --- | --- | --- |
| A | Sham Vehicle | — | 5 | — | 5 |
| B | Bleomycine induced fibrosis in animals treated with Vehicle | — | 5 | — | 5 |
| C | Bleomycine induced fibrosis in animals treated with Compound I-4×HCl | 30 | 5 | 30 | 5 |

Measurement of Lung Oedema

The wet lung weight was measured 7 days after BLM injection by careful excision of the lung from other adjacent extraneous tissues. The lung was then exposed for 48 h to 180° C. and the dry weight measured. Water content was then calculated by subtracting the dry weight from the wet weight.

Histological Examination

Lung biopsies were taken 7 days after BLM injection. After fixation at room temperature in buffered formaldehyde solution (10% in phosphate buffered saline [PBS]), the sections were prepared and stained by haematoxylin-eosin and observed with an Axiovision Zeiss microscope (Milan, Italy).

Scoring for lung fibrosis was graded on a scale from 0 to 8 by examining randomly chosen sections, with 5 fields per sample at a magnification of ×100. Criteria for grading lung fibrosis were as follows: grade 0, normal lung; grade 1, minimal fibrous thickening of alveolar or bronchiolar walls; grade 3, moderate thickening of walls without obvious damage to lung architecture; grade 5, increased fibrosis with definite damage to lung structure and formation of fibrous bands or small fibrous masses; grade 7, severe distortion of structure and large fibrous areas; and grade 8, total fibrous obliteration of fields (Cuzzocrea S, et al. *Am J Physiol Lung Cell Mol Physiol*. (2007) 292:L1095-104).

Myeloperoxidase (MPO) Assay

Myeloperoxidase (MPO) activity was determined 7 days after BLM injection. The lung was removed, weighed, homogenized in a solution containing 0.5% hexa-decyl-trimethyl-ammonium bromide dissolved in 10 mM potassium phosphate buffer (pH 7) and centrifuged for 30 min at 20,000 g at 4° C. An aliquot of the supernatant was then allowed to react with a solution of tetra-methyl-benzidine (1.6 mM) and 0.1 mM $H_2O_2$. The rate of change in absorbance was measured spectrophotometrically at 650 nm. MPO activity was defined as the quantity of enzyme degrading 1 µmol of peroxide per min at 37° C. and was expressed in units per gram weight of wet tissue.

Measurement of Thiobarbituric Acid-reactant Substances

Thiobarbituric acid-reactant substances (TBARS) measurement, which is considered a good indicator of lipid peroxidation, was determined in the lung tissues collected at 7 days after BLM administration. Lung tissues collected at the specified time were homogenized in 1.15% KC solution. A 100 µl aliquot of the homogenate was added to a reaction mixture containing 200 µl of 8.1% sodium dodecyl sulfate (SDS), 1.5 ml of 20% acetic acid (pH 3.5), 1.5 ml of 0.8% thiobarbituric acid and 600 µl distilled water. Samples were then boiled for 1 h at 95° C. and centrifuged at 3,000 g for 10 min. The absorbance of the supernatant was measured spectrophotometrically at 650 nm. Levels of TBARS are expressed as µM/100 mg of wet tissue.

Measurement of Cytokines

TNF-α and IL-1β levels were evaluated from lung tissues collected at 7 days after BLM administration. Briefly, portions of lung tissues were homogenized in phosphate-buffered saline (PBS, ICN Biomedicals, Milan, Italy) containing 2 mmol/L of phenyl-methyl sulfonyl fluoride (PMSF, Sigma-Aldrich Ltd.). The assay was carried out using a colorimetric commercial kit (R&D system Milan, Italy) according to the manufacturer's instructions. All cytokine determinations were performed in duplicate serial dilutions.

Immunohistochemical Localization for INOS, COX-2, Nitrotyrosine, TGF-β and PAR

At 7 days after BLM administration, lung tissues were fixed in 10% PBS-buffered formaldehyde and 7 µm sections were prepared from paraffin-embedded tissues. After deparaffinization, endogenous peroxidase was quenched with 0.3% hydrogen peroxide in 60% methanol for 30 min. The sections were permeabilized with 0.1% Triton X-100 in PBS for 20 min. Non-specific adsorption was minimized by incubating the section in 2% normal goat serum in PBS for 20 min. Endogenous biotin or avidin binding sites were blocked by sequential incubation for 15 min with biotin and avidin (Vector Laboratories, Burlingame, Calif.), respectively. Sections were incubated overnight with: 1) purified polyclonal antibody directed towards iNOS (Santa Cruz Biotechnology, 1:500 in PBS); or 2) with purified anti-COX-2 (Santa Cruz Biotecnology 1:500 in PBS); or 3) with anti-nitrotyrosine rabbit polyclonal antibody (Upstate, 1:500 in PBS); or 4) with anti-TGF-β-polyclonal antibody (Santa Cruz, 1:500 in PBS); or 5) anti-PAR antibody (BioMol, 1:200 in PBS). Sections were washed with PBS, and incubated with secondary antibody. Specific labeling was detected with a biotin-conjugated goat anti-rabbit IgG and avidin-biotin peroxidase complex (DBA). To verify the binding specificity for nitrotyrosine, PAR, TGF-β, COX-2 and iNOS, some sections were also incubated with only the primary antibody (no secondary) or with only the secondary antibody (no primary). In these situations no positive staining was found in the sections, indicating that the immunoreactions were positive in all the experiments carried out.

Observations

At the time of routine monitoring, the animals were checked for any effects of acute lung injury and treatments on normal behavior such as mobility, food and water consumption (by looking only), body weight gain/loss (body weights were measured daily), eye/hair matting and any other abnormal effect. Death and observed clinical signs were recorded on the basis of the numbers of animals within each subset.

Statistical Evaluation

All data in the text are presented as mean±s.e. mean of n observations, where n represents the number of animals studied. All statistical analysis was calculated using GraphPad Prism 5 (GraphPad Software, San Diego, Calif., USA). Data without repeated measurements were assessed by a Mann-Whitney U t-test. Data with repeated measurements were assessed by a two-way ANOVA followed by a Bonferroni post-hoc test. A P-value of less than 0.05 was considered to be statistically significant.

Results

TABLE 2

Histological fibrosis score

| | Group | | |
|---|---|---|---|
| Mouse | SHAM + Vehicle | BLM + Vehicle | BLM + Treatment with Compound I-4 × HCl |
| 1 | 0.0 | 7.2 | 2.0 |
| 2 | 0.0 | 6.5 | 1.0 |
| 3 | 0.0 | 6.0 | 3.0 |
| 4 | 0.0 | 7.0 | 2.0 |
| 5 | 0.0 | 7.0 | 3.0 |
| 6 | 0.0 | 8.0 | 3.0 |
| 7 | 0.0 | 7.0 | 2.0 |
| 8 | 0.0 | 8.0 | 2.0 |
| 9 | 0.0 | 7.0 | 3.0 |
| 10 | 0.0 | 7.0 | 3.0 |
| Mean | 0.0 | 7.07 | 2.40 |

Treatment with the compound I-4×HCl (4-[(4-Methoxyphenyl)amino]-6-(methylcarbamoyl)-quinoline-3-carboxylic acid hydrochloride) at a dose of 30 mg/kg 30 min after intra-tracheal instillation of BLM and every 12 h thereafter until completion of the study resulted in significant attenuation of histological scoring of fibrosis, acute lung injury, weight loss, lung inflammation and lung oedema.

The levels of various fibrotic markers were measured in the three groups (A, B and C). For each marker, the level measured in the bleomycin-injured, vehicle-treated group (BLM+Vehicle) was taken as 100%. In Table 3, the corresponding marker levels for the "sham injured" group treated with vehicle (Sham+Vehicle), and the bleomycin-injured group treated with compound I-4 (BLM+I-4×HCl), are indicated as a percentage of the level in the BLM+Vehicle group.

TABLE 3

Fibrotic marker levels

| Marker | BLM + Vehicle | Sham + Vehicle | BLM + I-4 × HCl |
|---|---|---|---|
| Histological score for lung acute injury | 100% | 0% (P < 0.0001) | 33% (P < 0.001) |
| Lung myeloperoxidase (MPO) | 100% | 7% (P < 0.0001) | 47% (P < 0.0001) |
| Wet/dry weight ratio (oedema) | 100% | 30% (P < 0.001) | 52% (P < 0.001) |
| Lung TBARS levels | 100% | 30% (P < 0.001) | 45% (P < 0.001) |
| Lung TNF-α levels | 100% | 28% (P < 0.001) | 45% (P < 0.001) |
| Lung IL-1β levels | 100% | 16% (P < 0.001) | 50% (P < 0.001) |
| iNOS* | 100% | 0% (P < 0.01) | 0.1% (P < 0.01) |
| COX-2* | 100% | 0% (P < 0.01) | 0.1% (P < 0.05) |

TABLE 3-continued

Fibrotic marker levels

| Marker | BLM + Vehicle | Sham + Vehicle | BLM + I-4 × HCl |
| --- | --- | --- | --- |
| Nitrotyrosine* | 100% | 0% ($P < 0.01$) | 0.1% ($P < 0.05$) |
| TGF-β* | 100% | 0% ($P < 0.01$) | 0.1% ($P < 0.05$) |
| Poly-ADP-ribose (PAR)* | 100% | 0% ($P < 0.01$) | 0.1% ($P < 0.05$) |

TBARS = thiobarbituric acid-reactant substances
iNOS = inducible nitric oxide
COX-2 = cyclooxygenase-2
TNF = tumor necrosis factor
IL = interleukin
*immunohistochemical localization The levels of the markers induced by bleomycin were statistically significantly reduced when the animals were treated with the compound I-4. The levels of some of the markers (iNOS, COX-2, Nitrotyrosine, TGF-β and poly-ADP-ribose (PAR) in the group treated with compound I-4 were reduced to levels similar to those of the sham group. These results indicate a potent anti-fibrotic and ant-inflammatory effect of the compound I-4.

Cell Adhesion Assay

The cell adhesion assay is used to study inhibition of cell attachment (adhesion) of fibrosblast or RPE cells retinal epithelium cells) or HUVEC (human umbilical endothelial cells) to fibronectin as an in vitro method to predict the anti-fibrotic effect in the eye and other organs.

48-well plates are coated with 10 μg/mL human fibronectin at +4° C. over night and then blocked 1 h at 37° C. with 2% BSA (Bovine serum albumin) in PBS (Phosphate-Buffered Saline).

Cells (mouse fibroblasts (3T3), human fibroblasts, human retinal epithelium cells (RPE), or cell line ARPE19, vascular endothelial cells, etc.) are washed 2 times with Buffer 3 (0.14 M NaCl, 4.7 mM KC, 0.65 mM $MgSO_4$, 1.2 mM $CaCl_2$, 10 mM Hepes pH 7.4), counted and diluted to appropriate concentration in Buffer 3. Cells are pre-incubated 30 minutes on ice with control substances (antibody or RGD peptide) or CLT-28643 at 2 times the desired final concentration.

The plates are washed 3 times with Buffer 3 and then 0.1 mL Buffer 3 is added to each well. Plates are placed on ice and cell solutions are added to the wells, 0.1 mL/well. Plates are transferred to 37° C. and incubated for 15, 30 or 60 minutes (one plate/time point). After indicated incubation time, plates are removed from 37° C. and cell solutions are discarded. Wells are carefully washed 2 times with Buffer 3 and 0.1 mL Substrate solution (3.75 mM p-nitrophenol-N-acetyl-beta-D-glucosamide, 0.25% Triton X-100, 0.05 M Sodium Citrate pH 5.0) is added to each well. Plates are stored at −20° C.

Detection of adhered cells: 50 μL from each well in the 48-well plates is transferred to wells in a 96-well plate and incubated at 37° C. for the appropriate time (30 minutes to 4 h depending on cell type). A standard curve is prepared at the same time using cell samples with known amounts of cells. The plate is developed by addition of 75 μL/well Developing buffer (45 mM Glycine, 4.5 mM EDTA ph 10.4) and absorbance at 405 nm is read.

The invention claimed is:

1. A method for the treatment of fibrosis, or a fibrosis-related disease, whereby a therapeutically effective amount of a compound which is 4-[(4-methoxyphenyl)-amino]-6-(methylcarbamoyl)quinoline-3-carboxylic acid, or a pharmaceutically acceptable salt thereof, is administered to a patient in need of such treatment.

2. The method according to claim 1, wherein the compound is 4-[(4-methoxyphenyl)amino]-6-(methylcarbamoyl)quinoline-3-carboxylic acid hydrochloride.

3. The method according to claim 1, wherein the fibrosis, or fibrosis-related disease, is a fibrotic disease affecting the lung, liver, kidney, skin, epidermis, endodermis, muscle, tendon, cartilage, heart, stomach, large intestine, small intestine, colon, uterus, nervous system, testis, adrenal gland, artery, vein, biliary tract, or eye.

4. The method according to claim 3, wherein the fibrotic disease is hepatic fibrosis.

5. The method according to claim 3, wherein the fibrotic disease is renal fibrosis.

6. The method according to claim 3, wherein the fibrotic disease is lung fibrosis.

7. The method according to claim 3, wherein the fibrotic disease is skin fibrosis.

8. The method according to claim 3, wherein the fibrotic disease is stomach and intestinal fibrosis.

9. The method according to claim 3, wherein the fibrotic disease is eye fibrosis.

10. The method according to claim 3, wherein the fibrotic disease is Lymphangioleiomyomatosis (LAM).

11. The method according to claim 3, wherein the fibrotic disease is associated with a surgical intervention.

12. The method according to claim 11, wherein the surgical intervention is selected from filtration surgery (trabeculectomy), laser trabeculoplasty, laser cyclophotocoagulation (cycloablation) for end-stage glaucoma, surgery for acute closed-angle glaucoma, drainage implants (tube shunts), deep sclerectomy, ex-press mini-shunt, trabectome surgery, iridotomy and iridectomy, canaloplasty and viscocanolostomy and goniotomy.

* * * * *